(12) United States Patent
Jeong et al.

(10) Patent No.: US 12,267,928 B2
(45) Date of Patent: Apr. 1, 2025

(54) APPARATUS AND METHOD FOR CONTROLLING AN IN-VEHICLE LIGHTING ENVIRONMENT

(71) Applicants: HYUNDAI MOTOR COMPANY, Seoul (KR); KIA CORPORATION, Seoul (KR)

(72) Inventors: Hae Seong Jeong, Busan (KR); Jung Seok Suh, Yongin-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 246 days.

(21) Appl. No.: 17/969,405

(22) Filed: Oct. 19, 2022

(65) Prior Publication Data

US 2023/0225032 A1    Jul. 13, 2023

(30) Foreign Application Priority Data

Jan. 13, 2022 (KR) .................. 10-2022-0004987

(51) Int. Cl.
| | |
|---|---|
| H05B 47/11 | (2020.01) |
| A61B 5/00 | (2006.01) |
| B60J 1/20 | (2006.01) |
| B60Q 3/70 | (2017.01) |
| B60Q 9/00 | (2006.01) |
| G06F 3/01 | (2006.01) |

(Continued)

(52) U.S. Cl.
CPC ............ *H05B 47/11* (2020.01); *A61B 5/4809* (2013.01); *B60J 1/2011* (2013.01); *B60Q 3/70* (2017.02); *B60Q 9/00* (2013.01); *G06F 3/013* (2013.01); *G06V 20/597* (2022.01); *H05B 47/125* (2020.01); *B60Q 2500/00* (2013.01)

(58) Field of Classification Search
CPC ...................................................... H05B 47/11
See application file for complete search history.

(56) References Cited

U.S. PATENT DOCUMENTS

| | | | | |
|---|---|---|---|---|
| 9,758,093 | B2 * | 9/2017 | Backes | ............... B60Q 3/00 |
| 10,940,790 | B1 * | 3/2021 | Mazuir | ............... B60Q 3/80 |
| 11,084,357 | B2 * | 8/2021 | Huber | ............... G02F 1/0121 |

(Continued)

FOREIGN PATENT DOCUMENTS

| | | | | |
|---|---|---|---|---|
| DE | 102015210887 A1 * | 9/2016 | ............ B60Q 3/00 |
| FR | 3088598 A1 * | 5/2020 | ............ B60K 35/00 |

*Primary Examiner* — Michael A Berns
(74) *Attorney, Agent, or Firm* — Lempia Summerfield Katz LLC (57) ABSTRACT

An apparatus for controlling an in-vehicle lighting environment includes: a passenger state determination unit that determines a state of a passenger using a gaze of the passenger photographed by a camera of a vehicle; a driving state determination unit that determines a driving state of the vehicle using an acceleration value measured by an acceleration sensor of the vehicle; an external environment state determination unit that determines an external environment state of the vehicle using an external illuminance value measured by an external illuminance sensor of the vehicle; and a lighting environment control unit that controls an illuminance and a color of a first light disposed inside the vehicle based on data determined by at least one determination unit among the passenger state, driving state, and external environment state determination units.

15 Claims, 6 Drawing Sheets

(51) Int. Cl.
*G06V 20/59* (2022.01)
*H05B 47/125* (2020.01)

(56) References Cited

U.S. PATENT DOCUMENTS

| | | | |
|---|---|---|---|
| 11,833,959 B1* | 12/2023 | Mazuir | ................... B60Q 3/80 |
| 2010/0014711 A1* | 1/2010 | Camhi | ................... B60K 35/00 |
| | | | 382/104 |
| 2020/0242380 A1* | 7/2020 | Darnaud | ................ G06V 20/59 |
| 2022/0305986 A1* | 9/2022 | Hirohashi | ................ B60Q 3/76 |
| 2023/0225032 A1* | 7/2023 | Jeong | .................... B60J 1/2016 |
| | | | 701/49 |

* cited by examiner

APPARATUS AND METHOD FOR CONTROLLING AN IN-VEHICLE LIGHTING ENVIRONMENT

CROSS-REFERENCE TO RELATED APPLICATION

This application claims priority to and the benefit of Korean Patent Application No. 10-2022-0004987 filed on Jan. 13, 2022, the disclosure of which is incorporated herein by reference in its entirety.

BACKGROUND

1. Field of the Disclosure

The present disclosure relates to an apparatus and method for controlling an in-vehicle lighting environment. More particularly, the present disclosure relates to an apparatus for controlling an in-vehicle lighting environment, the apparatus configured to provide an optimal lighting environment to a passenger of an autonomous vehicle, and to a method using the same.

2. Discussion of Related Art

The content described in this section is merely to provide background information on the present disclosure and may not constitute prior art.

In order to improve the aesthetics of a vehicle and convenience of a passenger, various lights, for example, an ambient light, are installed inside a vehicle. In general, the ambient light is configured to emit light generated from a light source so that the passenger may experience a light having a soft color.

Such an ambient light may change the color or illuminance of the light according to a selection of the passenger, thereby changing the atmosphere inside the vehicle in various ways. However, ambient lighting currently on the market may merely change the color or illuminance of the light in order to improve the aesthetics. Further, most of the related art technologies merely inform a driver of the suggestion of driving-related information assuming that the driver is present in the vehicle.

In the case of an autonomous vehicle, since driving is not required, the passenger may perform various tasks and may also rest and sleep. For example, in a vehicle such as a robo-taxi, which carries only a passenger without a driver, apparatuses for interior lighting environments as well as the ambient light cannot provide a lighting environment optimized for the passenger.

SUMMARY

The purpose of the present disclosure is to provide an optimal lighting environment to a passenger according to a state of the passenger, an external environment, or the like of an autonomous vehicle.

According to at least one embodiment, the present disclosure provides an apparatus for controlling an in-vehicle lighting environment. The apparatus includes: a passenger state determination unit that determines a state of a passenger using a gaze of the passenger photographed by a camera of a vehicle; a driving state determination unit that determines a driving state of the vehicle using an acceleration value measured by an acceleration sensor of the vehicle; an external environment state determination unit that determines an external environment state of the vehicle using an external illuminance value measured by an external illuminance sensor of the vehicle; and a lighting environment control unit that controls an illuminance and a color of a first light disposed inside the vehicle based on data determined by at least one determination unit among the passenger state determination unit, the driving state determination unit, and the external environment state determination unit.

According to another embodiment, the present disclosure provides a vehicle comprising the above-described apparatus for controlling an in-vehicle lighting environment.

According to another embodiment, the present disclosure provides a method of controlling an apparatus for controlling an in-vehicle lighting environment. The method includes a data reception operation of receiving data on at least one state from among a passenger state determined using a gaze of a passenger photographed by a camera of a vehicle, a driving state determined using an acceleration value measured by an acceleration sensor of the vehicle, and an external environment state determined using an external illuminance value measured by an external illuminance sensor of the vehicle. The method also includes a control operation of controlling an illuminance and a color of a first light inside the vehicle based on the received data.

BRIEF DESCRIPTION OF THE DRAWINGS

The above and other objects, features, and advantages of the present disclosure should become more apparent to those of ordinary skill in the art through the following description of embodiments thereof with reference to the accompanying drawings, in which.

DETAILED DESCRIPTION OF EMBODIMENTS

Embodiments of the present disclosure are described below with reference to the accompanying drawings. In the following description, like reference numerals designate like elements, although the elements are shown in different drawings. Further, in the following description of some embodiments, a detailed description of known functions and configurations incorporated herein has been omitted for the purpose of clarity and for brevity.

Additionally, alphanumeric codes such as first, second, i), ii), a), b), etc., in numbering components are used solely for the purpose of differentiating one component from the other but not to imply or suggest the substances, the order, or sequence of the components. Throughout this specification, when parts "include" or "comprise" a component, they are meant to further include other components, not exclude other components unless there is a particular description contrary thereto. When a component, device, element, or the like of the present disclosure described as having a purpose or performing an operation, function, or the like, the component, device, or element should be considered herein as being "configured to" meet that purpose or perform that operation or function.

Figure 1:
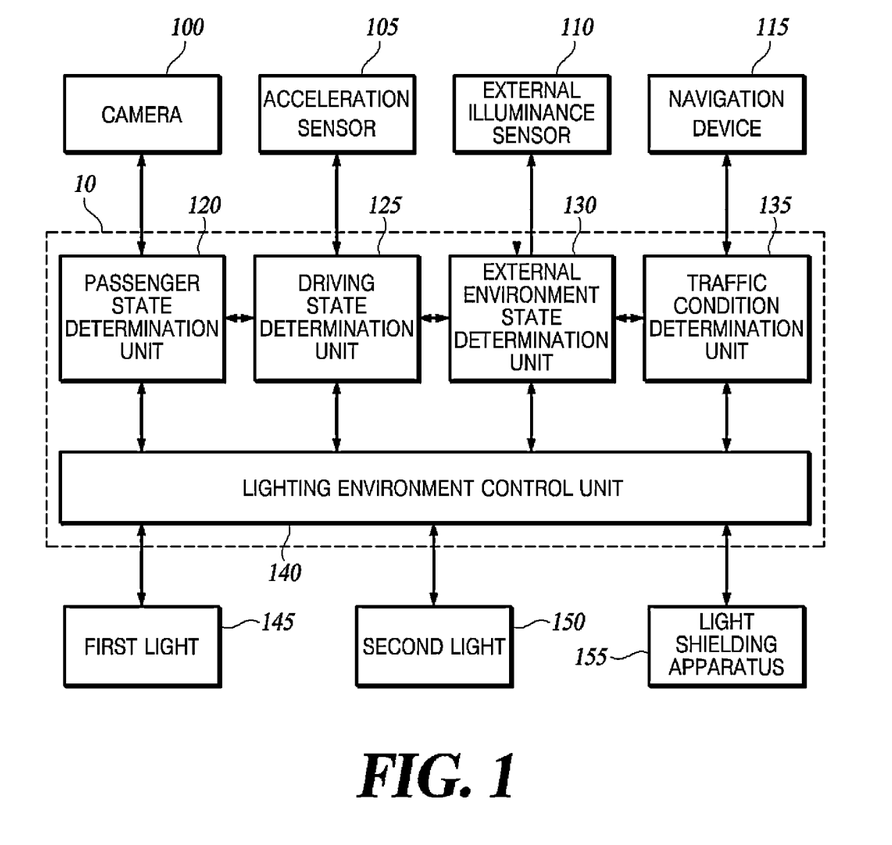
FIG. 1 is a block diagram illustrating an apparatus for controlling an in-vehicle lighting environment and a vehicle including the same according to an embodiment of the present disclosure.

FIG. 1 is a block diagram illustrating an apparatus for controlling an in-vehicle lighting environment and a vehicle including the same according to an embodiment of the present disclosure.

Figure 2:
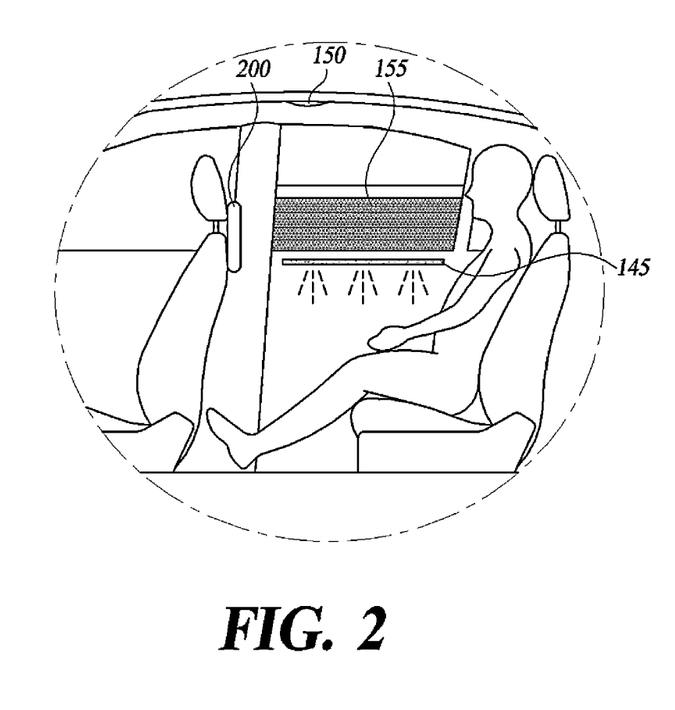
FIG. 2 is a view illustrating an example of a first light, a second light, and a light shielding apparatus of the vehicle including the apparatus for controlling the in-vehicle lighting environment according to the embodiment of the present disclosure.

FIG. 2 is a view illustrating an example of a first light, a second light, and a light shielding apparatus of the vehicle including the apparatus for controlling the in-vehicle lighting environment according to the embodiment of the present disclosure.

Referring to FIGS. 1 and 2, an integrated control unit 10 according to the embodiment of the present disclosure includes all or some of a passenger state determination unit 120, a driving state determination unit 125, an external environment state determination unit 130, a traffic condition determination unit 135, and a lighting environment control unit 140.

The passenger state determination unit 120 determines a state of the passenger using a gaze of the passenger photographed by a camera 100 of the vehicle. The state of the passenger may be classified into, for example, a sleep mode, a rest mode, an external gaze mode, a concentration mode, or the like. However, the state of the passenger is not necessarily classified into these four modes.

The passenger state determination unit 120 may determine that the state is the rest mode when the gaze of the passenger is unclear or the gaze cannot be determined. For example, when the passenger closes his/her eyes, the camera 100 cannot photograph the gaze of the passenger. Thus, in this case, the passenger state determination unit 120 may determine that the state of the passenger is the rest mode.

Further, the passenger state determination unit 120 may determine that the state of the passenger is the concentration mode when the gaze of the passenger to the outside of the vehicle does not deviate from a predetermined range for a preset period of time. For example, when the passenger looks at the scenery outside the vehicle, the gaze of the passenger photographed by the camera 100 may not move within a narrow range for a predetermined time.

The passenger state determination unit 120 may determine that the state of the passenger is the external gaze mode when the gaze of the passenger to the outside of the vehicle does not deviate from a predetermined range, for example, for about three minutes. However, the predetermined time is not necessarily limited to the three minutes.

Further, the passenger state determination unit 120 may determine that the state of the passenger is the concentration mode when the gaze of the passenger to the inside of the vehicle does not deviate from a predetermined range for a preset period of time. For example, when the passenger reads a book, the gaze of the passenger photographed by the camera 100 may not move within a narrow range for a predetermined time.

The passenger state determination unit 120 may determine that the state of the passenger is the concentration mode when the gaze of the passenger to the inside of the vehicle does not deviate from a predetermined range, for example, for about three minutes. However, the predetermined time is not necessarily limited to the three minutes.

Further, the passenger state determination unit 120 may determine that the state of the passenger is the sleep mode when an input of the sleep mode is received from the passenger. For example, the passenger may select the sleep mode on a separate input means 200 provided in the vehicle, for example, on a display panel. In this case, the passenger state determination unit 120 may determine that the state of the passenger is the sleep mode.

It has been described that only the sleep mode may be separately input from the passenger, but the present disclosure is not limited thereto. The passenger may select one mode among the rest mode, the external gaze mode, and the concentration mode in addition to the sleep mode using the input means 200 regardless of the gaze of the passenger. In this case, the passenger state determination unit 120 may prioritize the determination according to the selection of the passenger rather than the determination using the gaze of the passenger.

Further, the passenger state determination unit 120 may continuously monitor the state of the passenger as long as the passenger remains in the vehicle. In other words, even after it is determined that the state of the passenger is any one mode, i.e., for example, the concentration mode, when it is determined that, for example, the passenger looks at the outside by continuously using the gaze of the passenger, the passenger state determination unit 120 may determine that the state of the passenger is the external gaze mode.

The driving state determination unit 125 determines a driving state of the vehicle using an acceleration value measured from an acceleration sensor 105 of the vehicle.

The acceleration sensor 105 may measure a transverse acceleration as well as a longitudinal acceleration of the vehicle. Here, the longitudinal direction of the vehicle means a direction from the rear side to the front side of the vehicle. Likewise, the transverse direction means a direction from one side to the other side of the vehicle.

The driving state determination unit 125 may set a plurality of acceleration/deceleration modes for preset ranges for longitudinal acceleration values of the vehicle and may determine that the driving state of the vehicle is any one acceleration/deceleration mode.

For example, the driving state determination unit 125 may determine that the driving state is a stable mode when the longitudinal acceleration value of the vehicle is in the range of 0 to 0.1 g (g=9.8 m/s2). The unit 125 may determine that the driving state is a low acceleration/deceleration mode when the longitudinal acceleration value is in the range of 0.1 g to 0.3 g. The unit 125 may determine that the driving state is an intermediate acceleration/deceleration mode when the longitudinal acceleration value is in the range of 0.3 g to 0.5 g. The unit 125 may determine that the driving state is a high acceleration/deceleration mode when the longitudinal acceleration value is in the range of 0.5 g to 1.0 g. The unit 125 may determine that the driving state is an anti-lock brake system (ABS) operation mode when the longitudinal acceleration value exceeds 1.0 g.

However, the above-described ranges are merely examples. These ranges may be set differently depending on a vehicle model. The acceleration/deceleration mode does not need to be necessarily classified into five modes.

Further, when the longitudinal acceleration value of the vehicle exceeds a preset value independently of the acceleration/deceleration mode, the driving state determination unit 125 may determine that the driving state is a warning mode.

The preset value may always be set to be constant. However, the driving state determination unit 125 may adjust the preset value differently according to the state of the passenger determined by the passenger state determination unit 120. For example, when the state of the passenger is the sleep mode, the preset value may be 1.0 g, and when the state of the passenger is the concentration mode, the preset value may be 0.5 g.

Further, when a transverse acceleration value of the vehicle exceeds a preset value, the driving state determination unit 125 may determine that the driving state is a rotation mode. The driving state may be a rotation mode, for example, when the vehicle is making a turn or sliding or spinning sideways. For example, when the transverse acceleration value of the vehicle exceeds 0.5 g, the driving state determination unit 125 may determine that the driving state is the rotation mode. The preset value is not necessarily limited to 0.5 g.

The driving state determination unit 125 may also determine whether the vehicle is turning left or right using the transverse acceleration.

The external environment state determination unit 130 determines an external environment state of the vehicle using an external illuminance value measured by an external illuminance sensor 110 of the vehicle.

For example, the external environment state determination unit 130 may determine whether the vehicle is driving in a bright place or a dark place using the external illuminance value.

The traffic condition determination unit 135 may determine a traffic condition on a driving route of the vehicle by using data obtained from a navigation device 115 of the vehicle. For example, it may be determined whether the traffic condition of a road on which the vehicle is currently driving is clear, smooth, or congested.

The lighting environment control unit 140 may control the illuminance and the color of a first light 145 to be changed on the basis of the data determined by at least one determination unit from among the passenger state determination unit 120, the driving state determination unit 125, the external environment state determination unit 130, and the traffic condition determination unit 135.

Further, the lighting environment control unit 140 may also control the illuminance of a second light 150, disposed inside the vehicle and above the passenger, to be changed and may control a light shielding apparatus 155 disposed on a window of the vehicle to cover or not cover the window.

The second light 150 may be, for example, a light of which only the illuminance may be adjusted, such as a reading lamp, but may be a light of which both the illuminance and the color may be adjusted, like the first light 145. In this case, the lighting environment control unit 140 may control the illuminance and the color of the second light 150 to be changed.

Meanwhile, the lighting environment control unit 140 may automatically control the first light 145, the second light 150, and the light shielding apparatus 155. However, it should be apparent that the control may be individually and manually performed by the passenger.

Hereinafter, a method is described in detail in which the lighting environment control unit 140 controls the first light 145, the second light 150, and the light shielding apparatus 155 according to the determination of the passenger state determination unit 120, the driving state determination unit 125, the external environment state determination unit 130, and the traffic condition determination unit 135. Hereinafter, the control of the lighting environment control unit 140 described below is merely an example. The first light 145, the second light 150, and the light shielding apparatus 155 may be controlled in a different manner from an example described below.

(1) Sleep Mode

When the passenger state determination unit 120 determines that the state of the passenger is the sleep mode, the lighting environment control unit 140 may control the illuminance of the first light 145 to an illuminance set for the sleep of the passenger. For example, the lighting environment control unit 140 may control the illuminance of the first light 145 to be minimized. The minimized illuminance value may be adjusted by the passenger and/or may be fixed to a preset value.

However, when the driving state determination unit 125 determines that the driving state is the warning mode, the illuminance of the first light 145 may be controlled to be maximized.

Further, the lighting environment control unit 140 may control the color of the first light 145 to be changed according to the acceleration/deceleration mode determined by the driving state determination unit 125.

For example, when the driving state determination unit 125 determines that the driving state of the vehicle is the stable mode, the lighting environment control unit 140 may control the color of the first light 145 to be green.

When the driving state determination unit 125 determines that the driving state of the vehicle is the low acceleration/deceleration mode, the lighting environment control unit 140 may control the color of the first light 145 to be yellow.

When the driving state determination unit 125 determines that the driving state of the vehicle is the intermediate acceleration/deceleration mode, the lighting environment control unit 140 may control the color of the first light 145 to be orange.

When the driving state determination unit 125 determines that the driving state of the vehicle is the high acceleration/deceleration mode, the lighting environment control unit 140 may control the color of the first light 145 to be red.

When the driving state determination unit 125 determines that the driving state of the vehicle is an ABS operation mode, the lighting environment control unit 140 may control the color of the first light 145 to be red and control light of the first light 145 to be flashing.

Meanwhile, the lighting environment control unit 140 may control power of the second light 150 to be turned off and control the light shielding apparatus 155 to cover the window.

However, when the driving state determination unit 125 determines that the driving state is the warning mode, the light shielding apparatus 155 may be controlled so as not to cover the window, and the power of the second light 150 may be controlled to be turned on.

As described above, the lighting environment control unit 140 may control at least one of the first light 145, the second light 150, and the light shielding apparatus 155 to provide a lighting environment optimized for the sleep of the passenger.

(2) Rest Mode

When the passenger state determination unit 120 determines that the state of the passenger is in the rest mode, the lighting environment control unit 140 may control the illuminance of the first light 145 to be changed to an illuminance set according to the external illuminance value. For example, the lighting environment control unit 140 may control the illuminance of the first light 145 to be decreased when the outside is dark and control the illuminance of the first light 145 to be increased when the outside is bright.

Further, when the driving state determination unit 125 determines that the driving state is the rotation mode, the lighting environment control unit 140 may control illuminance of a first side light disposed on one side of the first light 145 and illuminance of a second side light disposed on the other side thereof in the vehicle to be different from each other. For example, the lighting environment control unit 140 may control illuminance of a first side light disposed on a side of the first light 145 in a direction in which the vehicle rotates to be higher than illuminance of a second side light disposed on a side in a direction opposite to the direction in which the vehicle rotates.

Further, the lighting environment control unit 140 may control the illuminance of the first light 145 to be changed according to a predetermined pattern. For example, the lighting environment control unit 140 may control the illuminance to be decreased or increased in a direction from the rear side to the front side of the vehicle or control the illuminance to be decreased or increased at preset time intervals.

The lighting environment control unit 140 may control the color of the first light 145 to be changed according to the acceleration/deceleration mode determined by the driving state determination unit 125. A detailed description thereof has been made in the sleep mode above and thus has been omitted here.

Meanwhile, the lighting environment control unit 140 may control the power of the second light to be turned off and control the illuminance of the second light 150 to be changed according to the external illuminance value when the power is turned on by the passenger. For example, the lighting environment control unit 140 may control the illuminance of the second light 150 to be decreased when the outside is dark and control the illuminance of the second light 150 to be increased when the outside is bright.

Further, the light shielding apparatus 155 is not controlled by the lighting environment control unit 140 and may be operated only by a manual operation of the passenger.

As described above, the lighting environment control unit 140 may control at least one of the first light 145, the second light 150, and the light shielding apparatus 155 to provide a lighting environment optimized for the rest of the passenger.

(3) External Gaze Mode

When the passenger state determination unit 120 determines that the state of the passenger is the external gaze mode, the lighting environment control unit 140 may control the illuminance of the first light 145 to be changed to an illuminance set according to the external illuminance value. For example, the lighting environment control unit 140 may control the illuminance of the first light 145 to be maintained at a brightness value of the early evening, for example, a value of about 100 lux when it is daytime or early evening. In another example, the lighting environmental control unit 40 may control the illuminance of the first light 145 to be maintained at a brightness value of the nighttime, for example, a value of about 10 lux when it is nighttime.

However, the illuminance of the first light 145 does not need to be necessarily changed to the illuminance set according to the external illuminance value and may be set by the passenger.

The lighting environment control unit 140 may control the color of the first light 145 to be changed according to the acceleration/deceleration mode determined by the driving state determination unit 125. A detailed description thereof has been made in the sleep mode above and thus has been omitted herein.

When the driving state determination unit 125 determines that the driving state is the rotation mode, the lighting environment control unit 140 may control the illuminance of the first side light disposed on the one side of the first light 145 and the illuminance of the second side light disposed on the other side thereof in the vehicle to be different from each other. Further, the lighting environment control unit 140 may control the power of the second light to be turned off and control the illuminance of the second light 150 to be changed according to the external illuminance value when the power is turned on by the passenger. A detailed description thereof has been made in the rest mode above and thus has been omitted here.

Meanwhile, when the light shielding apparatus 155 covers the window, for example, when a previous mode is the concentration mode or the passenger manually operates the light shielding apparatus 155 to cover the window, the lighting environment control unit 140 may control the light shielding apparatus 155 so as not to cover the window.

As described above, the lighting environment control unit 140 may control at least one of the first light 145, the second light 150, and the light shielding apparatus 155 to provide a lighting environment optimized for the external gaze of the passenger.

(4) Concentration Mode

When the passenger state determination unit 120 determines that the state of the passenger is the concentration mode, the lighting environment control unit 140 may control the illuminance of the first light 145 to be changed to an illuminance set for concentration of the passenger. For example, the lighting environment control unit 140 may control the illuminance of the first light 145 to be maintained at the brightness value of the early evening, for example, at about 100 lux.

Further, the lighting environment control unit 140 may control the illuminance of the second light 150 to be increased to the maximum.

However, when the driving state determination unit 125 determines that the driving state is in the warning mode, the lighting environment control unit 140 may control the illuminance of the first light 145 to be increased to the maximum and the second light 150 to be flashing while reducing the illuminance of the second light 150.

The lighting environment control unit 140 may control the color of the first light 145 to be changed according to the acceleration/deceleration mode determined by the driving state determination unit 125. A detailed description thereof has been made in the sleep mode above and thus has been omitted here.

Further, when the driving state determination unit 125 determines that the driving state is the rotation mode, the lighting environment control unit 140 may control the illuminance of the first side light disposed on the one side of the first light 145 and the illuminance of the second side light disposed on the other side thereof in the vehicle to be different from each other. A detailed description thereof has been made in the rest mode above and thus has been omitted here.

Meanwhile, the lighting environment control unit 140 may control the light shielding apparatus 155 to cover the window to improve the concentration of the passenger.

However, when the driving state determination unit 125 determines that the driving state is the warning mode, the lighting environment control unit 140 may control the light shielding apparatus 155 so as not to cover the window so that the passenger may identify an external situation. Regardless of the determination of the driving state determination unit 125, it should be apparent that the passenger may directly manually prevent the light shielding apparatus 155 from covering the window.

As described above, the lighting environment control unit 140 may control at least one of the first light 145, the second light 150, and the light shielding apparatus 155 to provide a lighting environment optimized for the concentration of the passenger.

Further, although not classified into a separate mode, when the traffic condition determination unit 135 determines that the traffic condition of the road is in a congested state, the lighting environment control unit 140 may control at least one of the first light 145, the second light 150, and the light shielding apparatus 155 in a preset manner in a congestion section.

Figure 3:
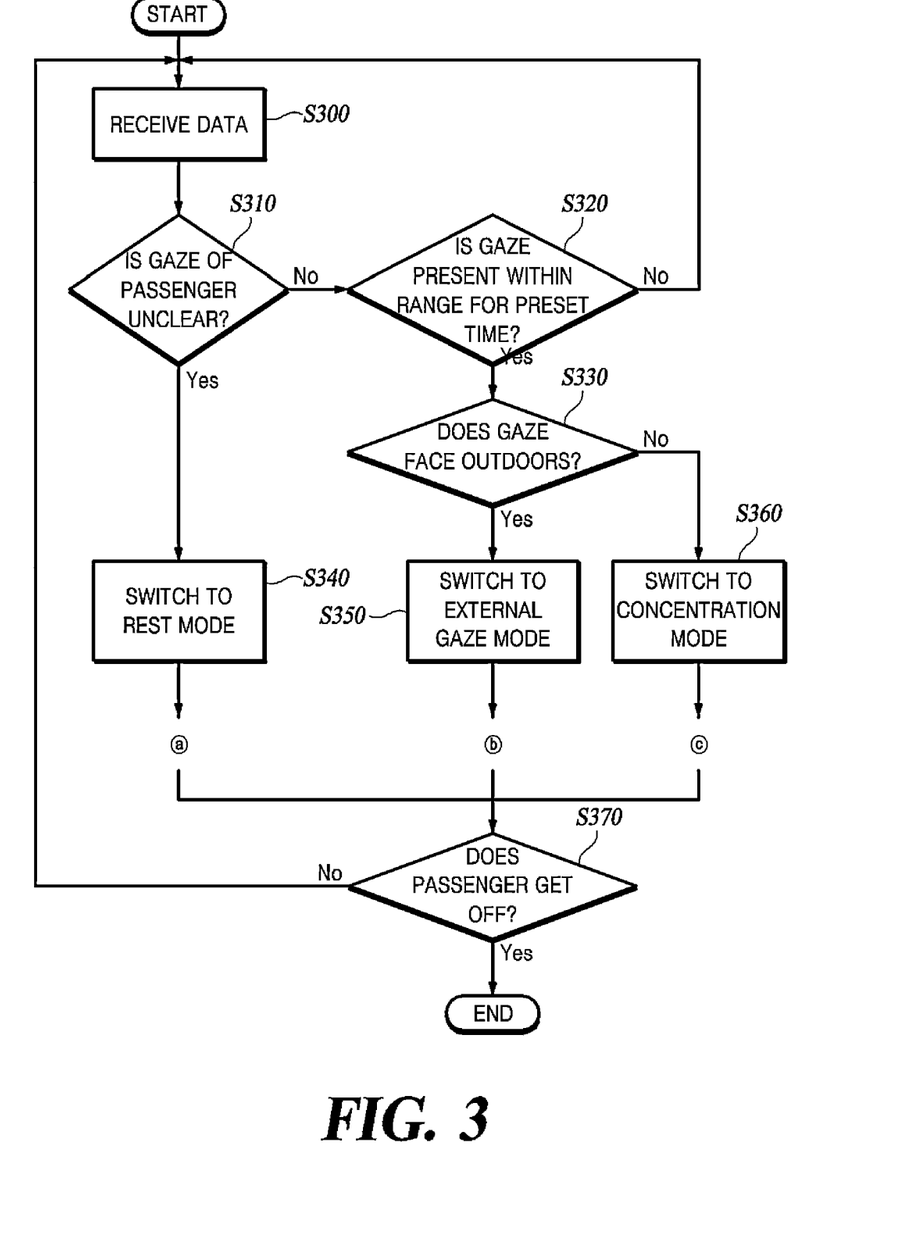
FIG. 3 is a flowchart illustrating a method of controlling an in-vehicle lighting environment according to the embodiment of the present disclosure.

FIG. 3 is a flowchart illustrating a method of controlling an in-vehicle lighting environment according to the embodiment of the present disclosure.

Referring to FIG. 3, the integrated control unit 10 receives data (S300). In this case, the data may be received from at least one of the camera 100, the acceleration sensor 105, the external illuminance sensor 110, and the navigation device 115. Thus, the integrated control unit 10 may receive data on at least one state among the passenger state, the driving state, the external environment state, and the road traffic state.

The integrated control unit 10 may control at least one of the first light 145, the second light 150, and the light shielding apparatus 155 on the basis of the received data. For example, the integrated control unit 10 may control the illuminance and the color of the first light 145, the illuminance of the second light 150, whether the light shielding apparatus 155 covers the window, and the like.

More specifically, the integrated control unit 10 determine whether the gaze of the passenger is unclear (S310). When it is determined that the gaze of the passenger is unclear, the integrated control unit 10 determines that the state of the passenger is in the rest mode (S340).

When it is determined that the gaze of the passenger is clear, the integrated control unit 10 determines whether the gaze of the passenger is present within a predetermined range for a preset time (S320). The preset time has been described above and thus a description thereof has been omitted here.

When it is determined that the gaze of the passenger is not present within the predetermined range for the preset time, the integrated control unit 10 continuously receives the data (S300). When it is determined that the gaze of the passenger is present within the predetermined range for the preset time, the integrated control unit 10 determines whether the gaze faces the outdoors (S330).

The integrated control unit 10 determines that the state of the passenger is the external gaze mode when it is determined that the gaze faces the outdoors (S350) and determines that the state of the passenger is the concentration mode when it is determined the gaze faces the indoors (S360).

When the control process according to each determined mode is performed, the integrated control unit 10 determines whether the passenger leaves, exits, or disembarks, i.e., gets off the vehicle (S370). When the passenger does not leave, exit, or disembark, i.e., get off the vehicle, the integrated control unit 10 continuously receives data (S300). When the passenger gets off the vehicle, the control process is terminated.

Meanwhile, in the control process illustrated in FIG. 3, it is illustrated that operation S310 is performed before operation S320 but the present disclosure is not limited thereto.

Operation S320 may be performed before operation S310 or both operations may be performed simultaneously.

Hereinafter, a control method according to each mode is described. However, the detailed control method in each mode may be the same as the above-described control method and thus a description thereof has been omitted here.

Figure 4:
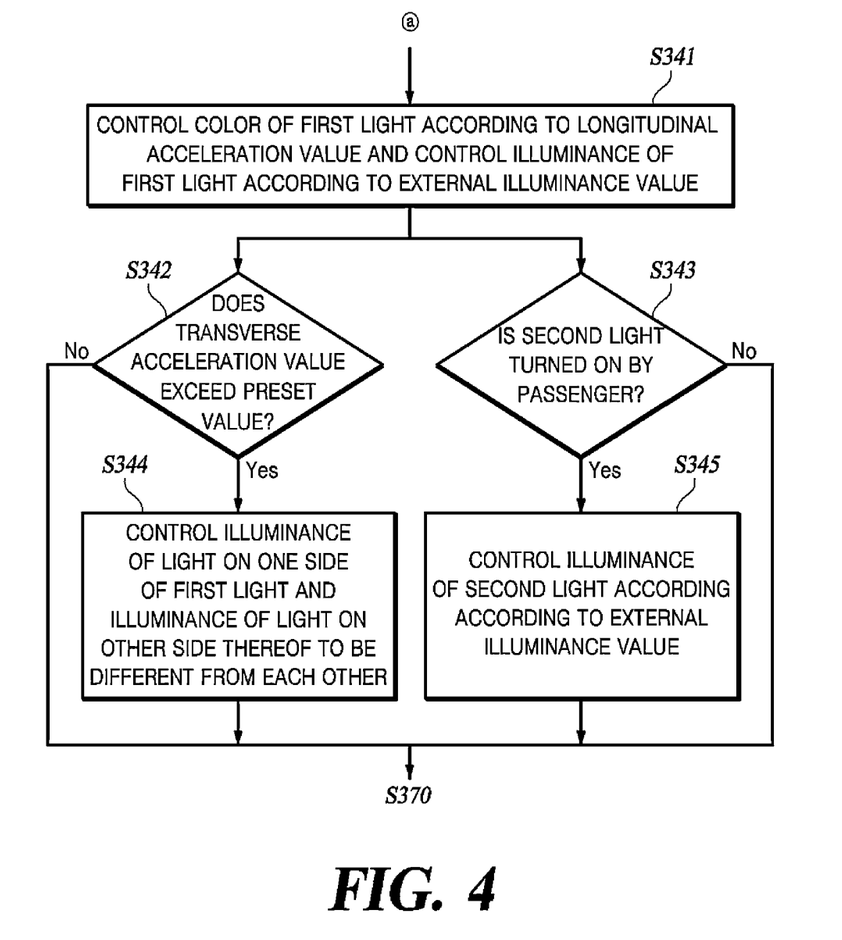
FIG. 4 is a flowchart illustrating a control method for a rest mode in FIG. 3 in detail.

FIG. 4 is a flowchart illustrating a control method for a rest mode in FIG. 3 in detail.

In the rest mode, the integrated control unit 10 controls the color of the first light 145 according to the longitudinal acceleration value and controls the illuminance of the first light 145 according to the external illuminance value (S341).

The integrated control unit 10 determines whether the transverse acceleration value exceeds the preset value (S342). When the transverse acceleration value exceeds the preset value, the integrated control unit 10 controls the illuminance of the first side light on the one side of the first light 145 and the illuminance of the second side light on the other side thereof to be different from each other (S344). When the transverse acceleration value does not exceed the preset value, operation S370 of determining whether the passenger gets off the vehicle is performed.

Further, the integrated control unit 10 determines whether the power of the second light 150 is turned on by the passenger (S343). When the power of the second light 150 is turned on, the integrated control unit 10 controls the illuminance of the second light 150 according to the external illuminance value (S345). When the power of the second light 150 is not turned on, operation S370 of determining whether the passenger gets off is performed.

The order of respective operations in FIG. 4 is merely an example. Operations S341, S342, and S343 may be performed in an order different from that in FIG. 4 or may be performed simultaneously.

Figure 5:
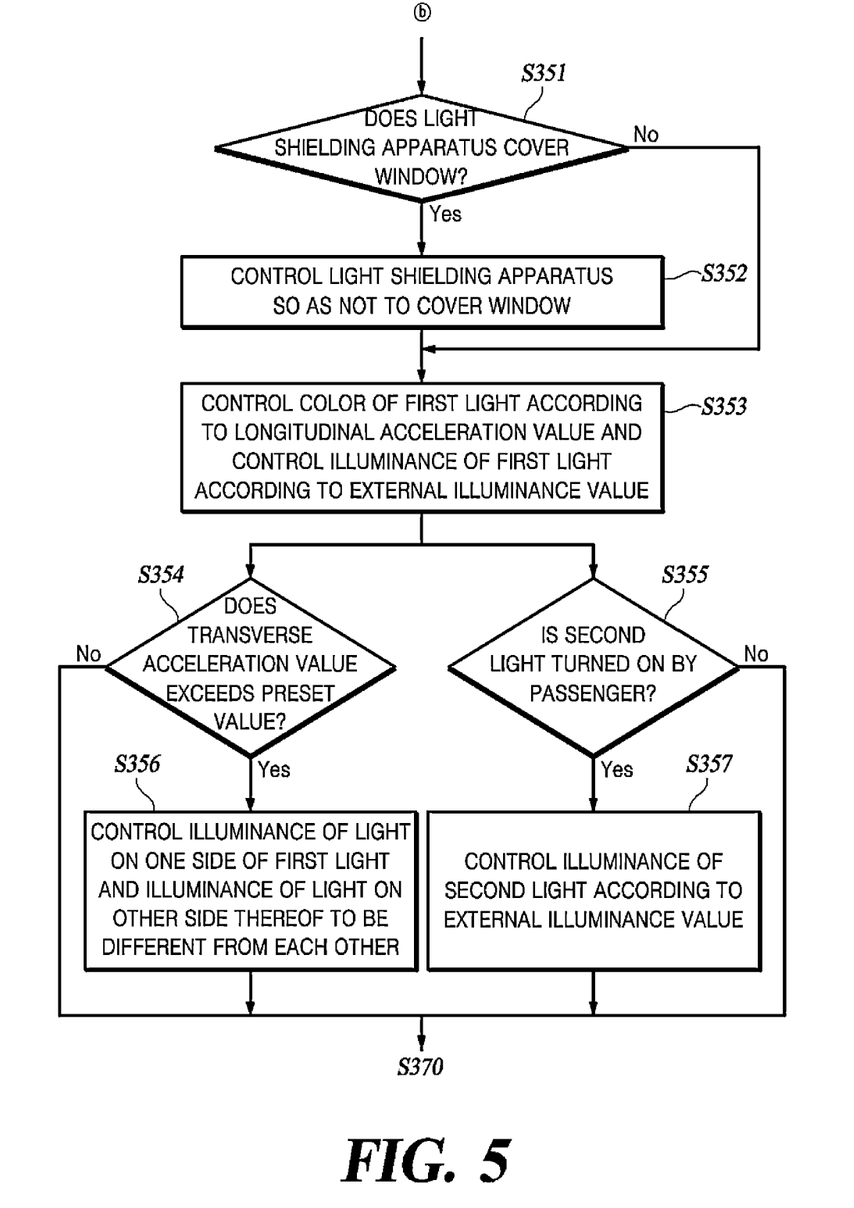
FIG. 5 is a flowchart illustrating a control method for an external gaze mode in FIG. 3 in detail.

FIG. 5 is a flowchart illustrating a control method for an external gaze mode in FIG. 3 in detail.

In the external gaze mode, the integrated control unit 10 determines whether the light shielding apparatus 155 covers the window (S351). When the light shielding apparatus 155 covers the window, the integrated control unit 10 controls the light shielding apparatus 155 so as not to cover the window (S352).

When the light shielding apparatus 155 does not cover the window, the integrated control unit 10 controls the color of the first light 145 according to the longitudinal acceleration value and controls the illuminance of the first light 145 according to the external illuminance value (S353).

The integrated control unit 10 determines whether the transverse acceleration value exceeds the preset value (S354). When the transverse acceleration value exceeds the preset value, the integrated control unit 10 controls the illuminance of the first side light on the one side of the first light 145 and the illuminance of the second side light on the other side thereof to be different from each other (S356). When the transverse acceleration value does not exceed the preset value, operation S370 of determining whether the passenger gets off the vehicle is performed.

Further, the integrated control unit 10 determines whether the power of the second light 150 is turned on by the passenger (S355). When the power of the second light 150 is turned on, the integrated control unit 10 controls the illuminance of the second light 150 according to the external illuminance value (S357). When the power of the second light 150 is not turned on, operation S370 of determining whether the passenger gets off is performed.

The order of respective operations in FIG. 5 is merely an example. Operations S351, S353, S354, and S355 may be performed in an order different from that in FIG. 5 or may be performed simultaneously.

Figure 6:
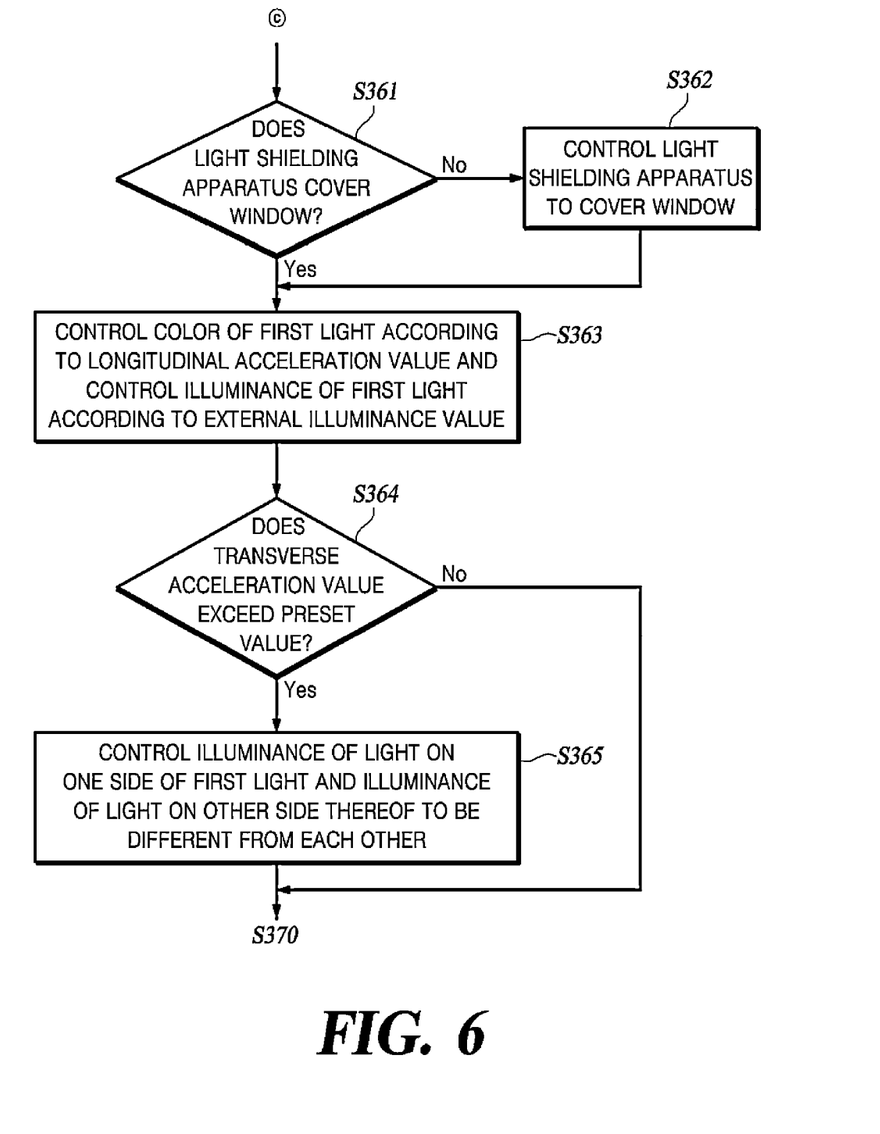
FIG. 6 is a flowchart illustrating a control method for a concentration mode in FIG. 3 in detail.

FIG. 6 is a flowchart illustrating a control method for a concentration mode in FIG. 3 in detail.

In the concentration mode, the integrated control unit 10 determines whether the light shielding apparatus 155 covers the window (S361). When the light shielding apparatus 155 does not cover the window, the integrated control unit 10 controls the light shielding apparatus 155 to cover the window (S362).

When the light shielding apparatus 155 covers the window, the integrated control unit 10 controls the color of the first light 145 according to the longitudinal acceleration value and controls the illuminance of the first light 145 according to the external illuminance value (S363).

The integrated control unit 10 determines whether the transverse acceleration value exceeds the preset value (S364). When the transverse acceleration value exceeds the preset value, the integrated control unit 10 controls the illuminance of the first side light on the one side of the first light 145 and the illuminance of the second side light on the other side thereof to be different from each other (S365). When the transverse acceleration value does not exceed the preset value, operation S370 of determining whether the passenger gets off the vehicle is performed.

The order of respective operations in FIG. 6 is merely an example. Operations S361, S363, and S364 may be performed in an order different from that in FIG. 6 or may be performed simultaneously.

Meanwhile, in the case of the sleep mode, although not illustrated, even in this case, the integrated control unit 10 may control the color of the first light 145 and controls the illuminance of the second light 150 according to the longitudinal acceleration value. Further, the integrated control unit 10 may determine whether the light shielding apparatus 155 covers the window and control the light shielding apparatus 155 to cover the window when the light shielding apparatus 155 does not cover the window. When the light shielding apparatus 155 covers the window, operation of determining whether the passenger gets off is performed.

According to the present embodiments, an optimal lighting environment can be provided for a passenger according to a state of the passenger, an external environment, or the like of an autonomous vehicle. In addition, a sickness of the passenger can be prevented and the passenger can prepare for an accident situation.

Although embodiments of the present disclosure have been described for illustrative purposes, those of ordinary skill in the art should appreciate that various modifications, additions, and substitutions are possible, without departing from the idea and scope of the claimed inventive concept. Therefore, embodiments of the present disclosure have been described for the sake of brevity and clarity. The scope of the technical idea of the present embodiments is not limited by the illustrations. Accordingly, one of ordinary skill in the art should understand the scope of the claimed invention is not to be limited by the above explicitly described embodiments but only by the claims and equivalents thereof.

REFERENCE NUMERALS

10: integrated control unit
100: camera
105: acceleration sensor
110: external illuminance sensor
115: navigation device -continued

REFERENCE NUMERALS

120: passenger state determination unit
125: driving state determination unit
130: external environment state determination unit
135: traffic condition determination unit
140: lighting environment control unit
145: first light
150: second light
155: light shielding apparatus
200: input means

What is claimed is:

1. An apparatus for controlling an in-vehicle lighting environment, the apparatus comprising:
a passenger state determination unit that determines a state of a passenger using a gaze of the passenger photographed by a camera of a vehicle;
a driving state determination unit that determines a driving state of the vehicle using an acceleration value measured by an acceleration sensor of the vehicle;
an external environment state determination unit that determines an external environment state of the vehicle using an external illuminance value measured by an external illuminance sensor of the vehicle; and
a lighting environment control unit that controls an illuminance and a color of a first light disposed inside the vehicle based on data determined by at least one determination unit among the passenger state determination unit, the driving state determination unit, and the external environment state determination unit,
wherein the passenger state determination unit determines that the state of the passenger is a rest mode when the gaze of the passenger is not identified, and
wherein the lighting environment control unit controls the illuminance of the first light to be changed to an illuminance set according to the external illuminance value when the passenger state determination unite determines that the state of the passenger is in the rest mode.

2. The apparatus of claim 1, wherein the driving state determination unit sets a plurality of acceleration/deceleration modes for preset ranges for a longitudinal acceleration value of the vehicle and determines that the driving state of the vehicle is in any one acceleration/deceleration mode, and
wherein the lighting environment control unit controls the color of the first light to be changed according to each acceleration/deceleration mode.

3. The apparatus of claim 1, wherein the driving state determination unit determines that the driving state of the vehicle is a rotation mode when a transverse acceleration value of the vehicle exceeds a preset value, and
wherein the lighting environment control unit controls illuminance of a first side light disposed on one side of the first light and illuminance of a second side light disposed on the other side thereof in the vehicle to be different from each other.

4. The apparatus of claim 1, wherein the passenger state determination unit determines that the state of the passenger is a concentration mode when the gaze of the passenger to an inside of the vehicle does not deviate from a predetermined range for a preset period of time, and
wherein the lighting environment control unit controls the illuminance of the first light to an illuminance set for concentration of the passenger when the passenger state determination unit determines that the state of the passenger is in the concentration mode.

5. The apparatus of claim 4, wherein the driving state determination unit determines that the driving state of the vehicle is a warning mode when a longitudinal acceleration value of the vehicle exceeds a preset value, and wherein the lighting environment control unit controls the illuminance of the first light to be increased to a maximum when the driving state determination unit determines that the driving state of the vehicle is in the warning mode.

6. The apparatus of claim 4, wherein the lighting environment control unit controls an illuminance of a second light disposed inside the vehicle and above the passenger to be increased to a maximum.

7. The apparatus of claim 6, wherein the driving state determination unit determines that the driving state of the vehicle is a warning mode when a longitudinal acceleration value of the vehicle exceeds a preset value, and wherein the lighting environment control unit controls the illuminance of the second light to be reduced and controls the second light to be flashing when the driving state determination unit determines that the driving state of the vehicle is in the warning mode.

8. The apparatus of claim 4, wherein the lighting environment control unit controls a light shielding apparatus disposed above a window of the vehicle to cover the window of the vehicle.

9. The apparatus of claim 1, wherein the passenger state determination unit determines that the state of the passenger is a sleep mode when an input of the sleep mode from the passenger is received, and wherein the lighting environment control unit controls the illuminance of the first light to an illuminance set for sleep of the passenger when the passenger state determination unit determines that the state of the passenger is in the sleep mode.

10. The apparatus of claim 9, wherein the driving state determination unit determines that the driving state of the vehicle is a warning mode when a longitudinal acceleration value of the vehicle exceeds a preset value, and wherein the lighting environment control unit controls the illuminance of the first light to be increased to a maximum when the driving state determination unit determines that the driving state of the vehicle is in the warning mode.

11. The apparatus of claim 9, wherein the lighting environment control unit controls a light shielding apparatus disposed above a window of the vehicle to cover the window of the vehicle.

12. The apparatus of claim 11, wherein the driving state determination unit determines that the driving state of the vehicle is a warning mode when a longitudinal acceleration value of the vehicle exceeds a preset value, and wherein the lighting environment control unit controls the light shielding apparatus so as not to cover the window of the vehicle when the driving state determination unit determines that the driving state of the vehicle is in the warning mode.

13. A vehicle comprising the apparatus for controlling an in-vehicle lighting environment according to claim 1.

14. An apparatus for controlling an in-vehicle lighting environment, the apparatus comprising:

a passenger state determination unit that determines a state of a passenger using a gaze of the passenger photographed by a camera of a vehicle;

a driving state determination unit that determines a driving state of the vehicle using an acceleration value measured by an acceleration sensor of the vehicle;

an external environment state determination unit that determines an external environment state of the vehicle using an external illuminance value measured by an external illuminance sensor of the vehicle;

a lighting environment control unit that controls an illuminance and a color of a first light disposed inside the vehicle based on data determined by at least one determination unit among the passenger state determination unit, the driving state determination unit, and the external environment state determination unit, wherein the passenger state determination unit determines that the state of the passenger is a concentration mode when the gaze of the passenger to an inside of the vehicle does not deviate from a predetermined range for a preset period of time or an external gaze mode when the gaze of the passenger to an outside of the vehicle does not deviate from a predetermined range for the preset period of time, wherein the driving state determination unit determines that the driving state of the vehicle is a warning mode when a longitudinal acceleration value of the vehicle exceeds a preset value, wherein the lighting environment control unit controls the illuminance of the first light to an illuminance set for concentration of the passenger and controls a light shielding apparatus disposed above a window of the vehicle to cover the window of the vehicle when the passenger state determination unit determines that the state of the passenger is in the concentration mode, and wherein the lighting environment control unit controls the light shielding apparatus so as not to cover the window of the vehicle when the driving state determination unit determines that the driving state of the vehicle is in the warning mode or when the passenger state determination unit determines that the state of the passenger is in the external gaze mode.

15. An apparatus for controlling an in-vehicle lighting environment, the apparatus comprising:

a passenger state determination unit that determines a state of a passenger using a gaze of the passenger photographed by a camera of a vehicle;

a driving state determination unit that determines a driving state of the vehicle using an acceleration value measured by an acceleration sensor of the vehicle;

an external environment state determination unit that determines an external environment state of the vehicle using an external illuminance value measured by an external illuminance sensor of the vehicle;

a lighting environment control unit that controls an illuminance and a color of a first light disposed inside the vehicle based on data determined by at least one determination unit among the passenger state determination unit, the driving state determination unit, and the external environment state determination unit, wherein the passenger state determination unit determines that the state of the passenger is an external gaze mode when the gaze of the passenger to an outside of the vehicle does not deviate from a predetermined range for a preset period of time, and wherein the lighting environment control unit controls the illuminance of the first light to be changed to an illuminance set according to the external illuminance value when the passenger state determination unit determines that the state of the passenger is in the external gaze mode.

* * * * *